(12) United States Patent
Schoenle et al.

(10) Patent No.: US 8,551,130 B2
(45) Date of Patent: Oct. 8, 2013

(54) THERAPEUTIC AGENT DELIVERY SYSTEM, DEVICE AND METHOD FOR LOCALIZED APPLICATION OF THERAPEUTIC SUBSTANCES TO A BIOLOGICAL CONDUIT

(75) Inventors: Victor Leo Schoenle, Greenfield, MN (US); Jody Lee Rivers, Elk River, MN (US); Jesse C. Darley, Madison, WI (US)

(73) Assignee: Cardiovascular Systems, Inc., St. Paul, MN (US)

( * ) Notice: Subject to any disclaimer, the term of this patent is extended or adjusted under 35 U.S.C. 154(b) by 130 days.

(21) Appl. No.: 13/027,391

(22) Filed: Feb. 15, 2011

(65) Prior Publication Data
US 2011/0202079 A1    Aug. 18, 2011

Related U.S. Application Data

(60) Provisional application No. 61/305,626, filed on Feb. 18, 2010.

(51) Int. Cl.
*A61B 17/22*    (2006.01)
(52) U.S. Cl.
USPC .......................................... 606/159; 606/194
(58) Field of Classification Search
USPC .................. 606/159, 170, 180, 192, 194; 604/103.01, 103.02, 509
See application file for complete search history.

(56) References Cited

U.S. PATENT DOCUMENTS

| | | |
|---|---|---|
| 4,700,705 A | 10/1987 | Kensey et al. |
| 4,747,821 A | 5/1988 | Kensey et al. |
| 4,790,813 A | 12/1988 | Kensey |
| 4,950,238 A | 8/1990 | Sullivan |
| 5,021,044 A | 6/1991 | Sharkawy |
| 5,261,877 A | 11/1993 | Fine et al. |
| 5,336,178 A | 8/1994 | Kaplan et al. |
| 5,626,562 A | 5/1997 | Castro |
| 5,681,336 A | 10/1997 | Clement et al. |
| 5,713,863 A | 2/1998 | Vigil et al. |
| 5,779,721 A | 7/1998 | Nash |
| 5,865,794 A | 2/1999 | Castro |
| 5,879,361 A | 3/1999 | Nash |
| 5,916,227 A * | 6/1999 | Keith et al. ................... 606/159 |

(Continued)

FOREIGN PATENT DOCUMENTS

WO    WO2009/096822    8/2009

OTHER PUBLICATIONS

International Search Report from related PCT application No. PCT/US2011/024967 dated Apr. 15, 2011.

*Primary Examiner* — Thomas McEvoy
(74) *Attorney, Agent, or Firm* — Winthrop & Weinstine, P.A.

(57) ABSTRACT

The invention provides a system, device and method for localized application of therapeutic substances within a biological conduit. One embodiment comprises a rotational atherectomy device having a flexible, elongated, rotatable, drive shaft having a lumen and with an eccentric enlarged abrading head having at least one application hole attached therethrough and in communication with a therapeutic agent delivery sheath and an operator-controlled actuator. The therapeutic substances may then spray radially outwardly from the application hole(s) on the eccentric abrading head during and/or after high-speed rotation of the head. Another embodiment comprises compartments in the abrading head that hold therapeutic agent(s) for release during high-speed rotation. In each case, the therapeutic substance(s) is delivered with radial forces resulting from high-speed orbital rotation of the eccentric abrading head, driving the therapeutic substance(s) into the conduit wall.

3 Claims, 12 Drawing Sheets

(56) References Cited

U.S. PATENT DOCUMENTS

| | | |
|---|---|---|
| 6,117,149 A | 9/2000 | Sorensen et al. |
| 6,183,487 B1 | 2/2001 | Barry et al. |
| 6,478,778 B1 | 11/2002 | Jacobsen et al. |
| 6,569,147 B1 | 5/2003 | Evans et al. |
| 6,830,577 B2 | 12/2004 | Nash et al. |
| 6,843,797 B2 | 1/2005 | Nash et al. |
| 2002/0198550 A1 | 12/2002 | Nash et al. |
| 2005/0149083 A1* | 7/2005 | Prudnikov et al. ............ 606/159 |
| 2005/0149084 A1* | 7/2005 | Kanz et al. .................... 606/159 |
| 2005/0240146 A1 | 10/2005 | Nash et al. |
| 2006/0253069 A1 | 11/2006 | Li et al. |
| 2006/0259005 A1 | 11/2006 | Konstantino et al. |
| 2008/0058763 A1 | 3/2008 | Boland et al. |
| 2008/0097499 A1 | 4/2008 | Nash et al. |
| 2008/0118561 A1 | 5/2008 | Nugent et al. |
| 2008/0188926 A1 | 8/2008 | Rea |
| 2008/0195042 A1 | 8/2008 | Weber |
| 2008/0287911 A1 | 11/2008 | El-Nounou et al. |
| 2009/0105687 A1 | 4/2009 | Deckman et al. |
| 2009/0299391 A1* | 12/2009 | Rivers et al. .................. 606/159 |
| 2010/0094320 A1 | 4/2010 | Arat et al. |

* cited by examiner

THERAPEUTIC AGENT DELIVERY SYSTEM, DEVICE AND METHOD FOR LOCALIZED APPLICATION OF THERAPEUTIC SUBSTANCES TO A BIOLOGICAL CONDUIT

BACKGROUND OF THE INVENTION

1. Field of the Invention

The invention relates to systems, devices and methods for treating biological conduits with localized delivery of therapeutic agents.

2. Description of the Related Art

A variety of techniques and instruments have been developed for use in the removal or repair of tissue in biological conduits, e.g., without limitation, blood vessels and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes, leg pain and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. The disclosure of U.S. Pat. No. 6,494,890 is hereby incorporated by reference in its entirety.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Another method of treatment of occluded vessels may include the use of stents. Stents may be placed at the site of a stenosis and expanded to widen the vessel, remaining in position as a vessel implant.

No matter the technique used to open an occluded conduit, e.g., blood vessel, and restore normal fluid flow therethrough, one problem remains: restenosis. A certain percentage of the treated conduits and vessels will reocclude (restenose) after a period of time; occurring in as many as 40-50% of the cases. When restenosis does occur, the original procedure may be repeated or an alternative method may be used to reestablish fluid, e.g., blood, flow.

The relevant commonality shared by each of the above treatment methods is that each one results in some trauma to the conduit wall. Restenosis occurs for a variety of reasons; each involving trauma. Small clots may form on the arterial wall. Small tears in the wall expose the blood to foreign material and proteins which are highly thrombogenic. Resulting clots may grow gradually and may even contain growth hormones released by platelets within the clot. Moreover, growth hormones released by other cells, e.g., macrophages, may cause smooth muscle cells and fibroblasts in the affected region to multiply in an abnormal fashion. There may be an injury in the conduit wall due to the above methods that results in inflammation which may result in the growth of new tissue.

It is known that certain therapeutic substances may have a positive effect on prevention and/or inhibition of restenosis. Several difficulties present themselves in the application of these substances to the affected region in a therapeutic dose. For example, the region in need of treatment is very small and localized. Fluid, e.g., blood, flow in the conduit is continuous, resulting in a flow boundary along the wall which must be disrupted so that the therapeutic substances may reach the localized region of interest within a dose range considered therapeutic. The art fails to adequately provide a mechanism for breaking through this flow boundary to target the region of interest; electing instead generally to place the therapeutic substance into the general flow of the conduit, either by intravenous means or intra-lumen infusion, at a dose that is much higher than therapeutic since the majority of the therapeutic substance will simply flow downstream and either be absorbed systemically or eliminated as waste. For example, intravenous medications are delivered systemically by vein, or regionally, e.g., through intra-lumen infusion without targeting the subject region. Such unnecessary systemic exposure results with unknown and unnecessary adverse results in regions, tissue, and/or organs that are distant from the region of interest. Clearly, systemic delivery and exposure is not well suited to treatment of diseases or conditions having a single intra-lumen region of interest.

The potential utility of localized application of a therapeutic dose of therapeutic substances is not limited to treatment of coronary arteries. Beyond coronary artery delivery, other sites of atherosclerosis, e.g., renal, iliac, femoral, distal leg and carotid arteries, as well as saphenous vein grafts, synthetic grafts and arterio-venous shunts used for hemodialysis would be appropriate biological conduits for a localized therapeutic substance delivery method and mechanism. Nor is the potential utility limited to blood vessels; any biological conduit having a region of interest amenable to treatment may benefit from such a treatment method and mechanism.

The present invention overcomes these deficiencies.

BRIEF SUMMARY OF THE INVENTION

The invention provides a system, device and method for localized application of therapeutic substances within a biological conduit. One embodiment comprises a rotational atherectomy device having a flexible, elongated, rotatable, drive shaft having a lumen and with an eccentric enlarged abrading head having at least one application hole attached therethrough and in communication with a therapeutic agent delivery sheath and an operator-controlled actuator. The therapeutic substances may then spray radially outwardly from the application hole(s) on the eccentric abrading head during and/or after high-speed rotation of the head. Another embodiment comprises compartments in the abrading head that hold therapeutic agent(s) for release during high-speed rotation. In each case, the therapeutic substance(s) is delivered with radial forces resulting from high-speed orbital rotation of the eccentric abrading head, driving the therapeutic substance(s) into the conduit wall.

In this manner, application of at least one therapeutic dose of the therapeutic substance(s) at the affected region is achieved using the radial forces supplied and generated by the high-speed rotation of the eccentric enlarged abrading head, while minimizing unwanted systemic exposure and the accompanying undesirable side effects. As a consequence, the need to administer super-therapeutic doses is eliminated.

An object of the invention is to provide a high-speed rotational atherectomy system, method and device for delivering a therapeutic dose of at least one therapeutic substance to an affected region on a biological conduit wall.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
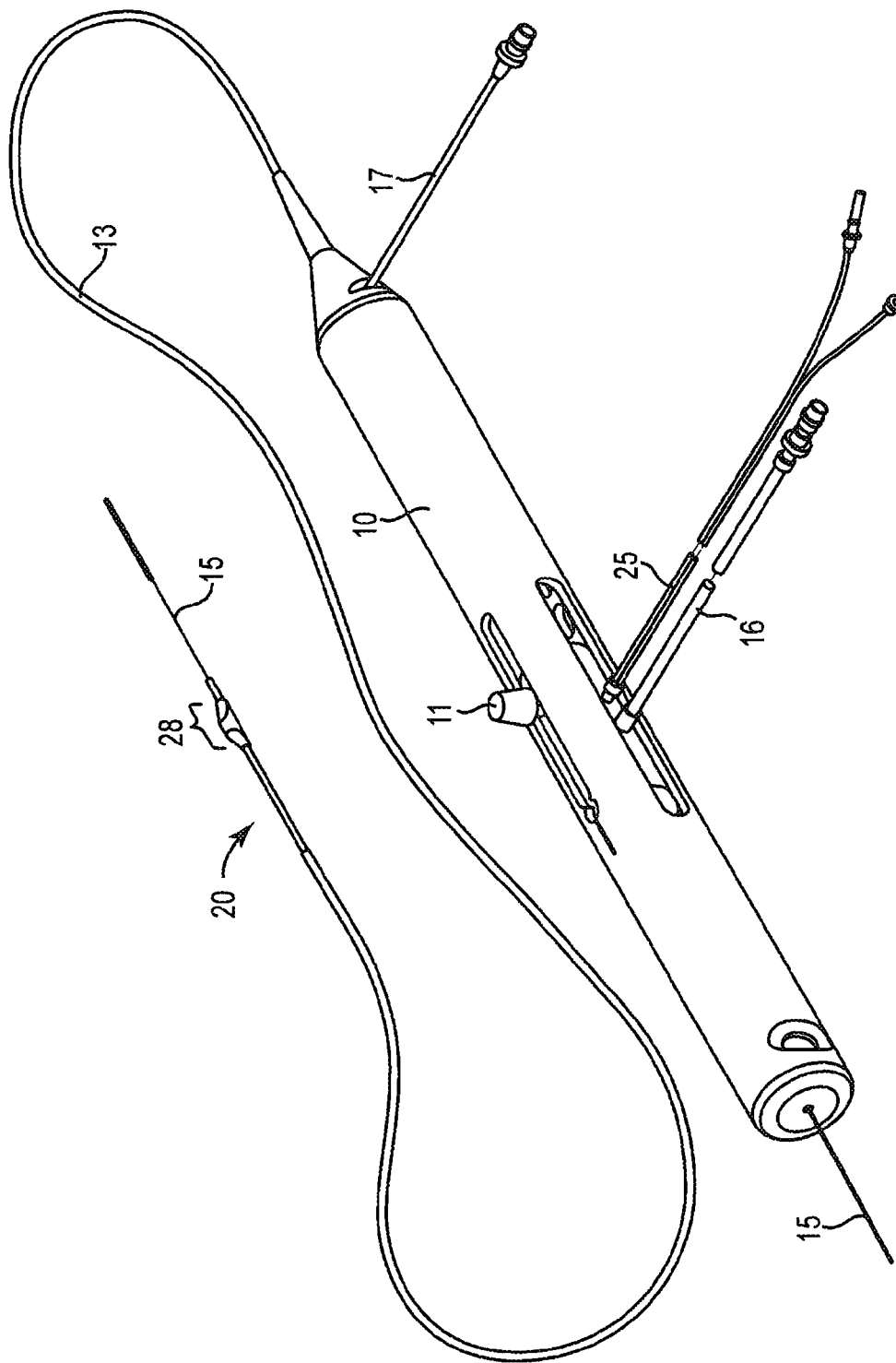
FIG. 1 is a perspective view of one embodiment of a therapeutic agent delivery system comprising an eccentric abrading head of a rotational atherectomy device of the invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

For the purposes of the present invention, the following terms and definitions apply:

"Bodily disorder" refers to any condition that adversely affects the function of the body.

The term "treatment" includes prevention, reduction, delay, stabilization, and/or elimination of a bodily disorder, e.g., a vascular disorder. In certain embodiments, treatment comprises repairing damage cause by the bodily, e.g., vascular, disorder and/or intervention of same, including but not limited to mechanical intervention.

A "therapeutic agent" comprises any substance capable of exerting an effect including, but not limited to therapeutic, prophylactic or diagnostic. Thus, therapeutic agents may comprise anti-inflammatories, anti-infectives, analgesics, anti-proliferatives, and the like including but not limited to antirestenosis drugs. Therapeutic agent further comprises mammalian stem cells. Therapeutic agent as used herein further includes other drugs, genetic materials and biological materials. The genetic materials mean DNA or RNA, including, without limitation, of DNA/RNA encoding a useful protein, intended to be inserted into a human body including viral vectors and non-viral vectors. Viral vectors include adenoviruses, gutted adenoviruses, adeno-associated virus, retroviruses, alpha virus, lentiviruses, herpes simplex virus, ex vivo modified cells (e.g., stem cells, fibroblasts, myoblasts, satellite cells, pericytes, cardiomyocytes, skeletal myocytes, macrophage), replication competent viruses, and hybrid vectors. Non-viral vectors include artificial chromosomes and minichromosomes, plasmid DNA vectors, cationic polymers, graft copolymers, neutral polymers PVP, SP1017, lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor .alpha. and .beta., platelet derived endothelial growth factor, platelet derived growth factor, tumor necrosis factor .alpha., hepatocyte growth factor and insulin like growth factor), transcription factors, proteinkinases, CD inhibitors, thymidine kinase, and bone morphogenic proteins. These dimeric proteins can be provided as homodimers, heterodimers, or combinations thereof, alone or together with other molecules.

Therapeutic agents further includes cells that can be of human origin (autologous or allogeneic) or from an animal source (xenogeneic), genetically engineered, if desired, to deliver proteins of interest at the transplant site. Cells within the definition of therapeutic agents herein further include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Therapeutic agent also includes non-genetic substances, such as: anti-thrombogenic agents such as heparin, heparin derivatives, and urokinase; anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as heparin, antithrombin compounds, platelet receptor antagonists, anti-thrombin anticodies, anti-platelet receptor antibodies, aspirin, dipyridamole, protamine, hirudin, prostaglandin inhibitors, platelet inhibitors and tick antiplatelet peptides; vascular cell growth promotors such as growth factors, Vascular Endothelial Growth Factors, growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme, inhibitors including captopril and analopril. The biologically active material can be used with (a) biologically non-active material(s) including a solvent, a carrier or an excipient, such as sucrose acetate isobutyrate, ethanol, n-methyl pymolidone, dimethyl sulfoxide, benzyl benxoate and benzyl acetate.

Further, "therapeutic agent" includes, in particular in a preferred therapeutic method of the present invention comprising the administration of at least one therapeutic agent to a procedurally traumatized, e.g., by an angioplasty or atherectomy procedure, mammalian vessel to inhibit restenosis. Preferably, the therapeutic agent is a cytoskeletal inhibitor or a smooth muscle inhibitor, including, for example, taxol and functional analogs, equivalents or derivatives thereof such as taxotere, paclitaxel, abraxane TM, coroxane TM or a cytochalasin, such as cytochalasin B, cytochalasin C, cytochalasin A, cytochalasin D, or analogs or derivatives thereof.

Additional specific examples of "therapeutic agents" that may be applied to a bodily lumen using various embodiments of the present invention comprise, without limitation:

L-Arginine;
Adipose Cells;
Genetically altered cells, e.g., seeding of autologous endothelial cells transfected with the beta-galactosidase gene upon an injured arterial surface;
Erythromycin;
Penicillin:
Heparin;
Aspirin;
Hydrocortisone;
Dexamethasone;
Forskolin;
GP IIb-IIIa inhibitors;
Cyclohexane;
Rho Kinsase Inhibitors;
Rapamycin;
Histamine;
Nitroglycerin;
Vitamin E;
Vitamin C;
Stem Cells;
Growth Hormones;
Hirudin;
Hirulog;

Argatroban;
Vapirprost;
Prostacyclin;
Dextran;
Erythropoietin;
Endothelial Growth Factor;
Epidermal Growth Factor;
Core Binding Factor A;
Vascular Endothelial Growth Factor;
Fibroblast Growth Factors;
Thrombin;
Thrombin inhibitor; and
Glucosamine, among many other therapeutic substances.

The therapeutic agent delivery system of the present invention can be used to apply the therapeutic agent to any surface of a body lumen where a catheter can be inserted. Such body lumen includes, inter alia, blood vessels, urinary tract, coronary vasculature, esophagus, trachea, colon, and biliary tract.

FIG. 1 illustrates one embodiment of a known high-speed rotational atherectomy system, elements of which are utilized in various embodiments of the present invention. The device includes a handle portion 10, an elongated, flexible drive shaft 20 having an eccentric enlarged abrading head 28, and an elongated catheter 13, illustrated with dashed lines, extending distally from the handle portion 10. The drive shaft 20 is constructed from helically coiled wire as is known in the art and the abrading head 28 is fixedly attached thereto. The catheter 13 has a lumen L within which the drive shaft 20 is slidably disposed and further comprises a distal end.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. Details regarding such handles and associated instrumentation are well known in the industry. The handle 10 also desirably includes a control knob 11 for advancing and retracting the turbine and drive shaft 20 with respect to the catheter 13 and the body of the handle.

Figure 2A:
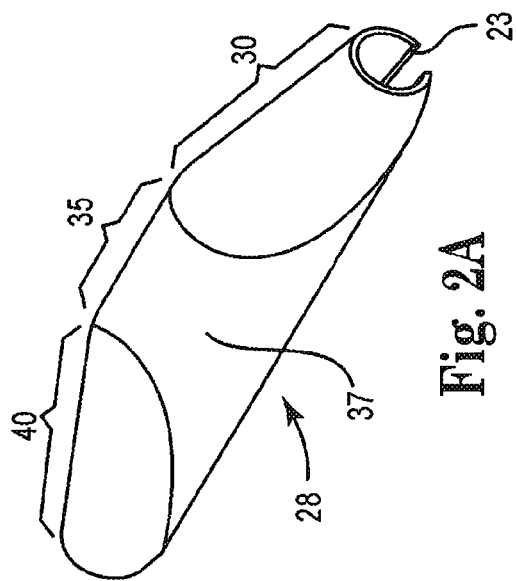
FIG. 2A is a perspective view of one embodiment of the eccentric abrading head of FIG. 1.
Figure 2B:
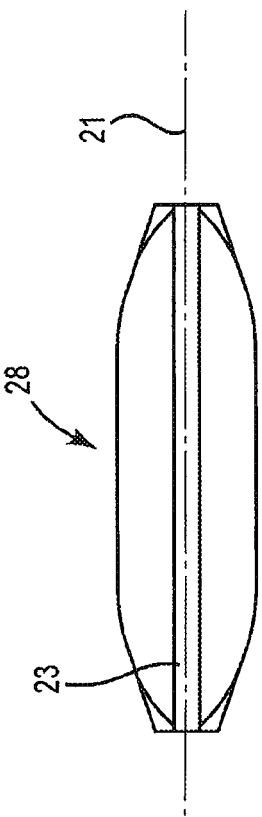
FIG. 2B is a bottom view of one embodiment of the eccentric abrading head of FIG. 1.
Figure 2C:
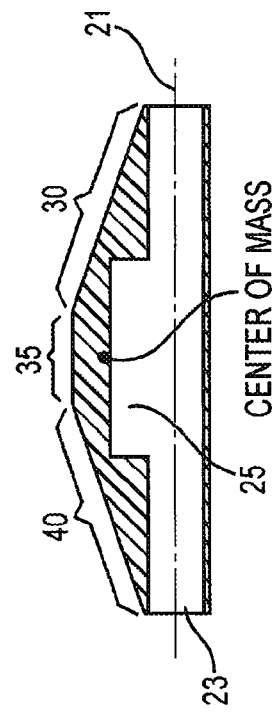
FIG. 2C is a longitudinal cross-section view of one embodiment of the eccentric abrading head of FIG. 1.

Turning now to FIGS. 2A, 2B and 2C, one embodiment of the eccentric enlarged abrading head 28 of the therapeutic agent delivery system of the invention will be discussed. The drive shaft 20 has a rotational axis 21 which is coaxial with the guide wire 15, the guide wire 15 being disposed within the lumen of the drive shaft 20 as illustrated in FIG. 1.

The abrading head 28 may comprise at least one tissue removing surface 37 on the external surface(s) of the intermediate portion 35, the distal portion 40 and/or the proximal portion 30 to facilitate abrasion of the stenosis during high speed rotation. The tissue removing surface 37 may comprise a coating of an abrasive material 24 bound to the external surface(s) of the intermediate portion 35, the distal portion 40 and/or the proximal portion 30 of abrading head 28. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the tissue removing surface(s) by a suitable binder—such attachment may be achieved using well known techniques, such as conventional electroplating or fusion technologies (see, e.g., U.S. Pat. No. 4,018,576). Alternately the external tissue removing surface may comprise mechanically or chemically roughening the external surface(s) of the intermediate portion 35, the distal portion 40 and/or the proximal portion 30 to provide a suitable abrasive tissue removing surface 37. In yet another variation, the external surface may be etched or cut (e.g., with a laser) to provide small but effective abrading surfaces. Other similar techniques may also be utilized to provide a suitable tissue removing surface 37.

An at least partially enclosed lumen or slot 23 may be provided longitudinally through the enlarged abrading head 28 along the rotational axis 21 of the drive shaft 20 for securing the abrading head 28 to the drive shaft 20 in a manner well known to those skilled in the art. In the embodiment shown, a hollowed section 25 is provided to lessen the mass of the abrading head 28 to facilitate atraumatic abrasion and improve predictability of control of the orbital pathway of the abrading head 28 during high speed, i.e., 20,000 to 200,000 rpm, operation. In this embodiment, the abrading head 28 may be fixedly attached to the drive shaft 20, wherein the drive shaft comprises one single unit. The size and shape of the hollowed section 25 may be modified to optimize the orbital rotational path of the abrading head 28 for particularly desirable rotational speeds. Those skilled in the art will readily recognize the various possible configurations, each of which is within the scope of the present invention. Other embodiments of the eccentric abrading head 28 may not comprise hollowed section 25.

The embodiment of FIGS. 2A-2C illustrates the proximal portion 30 and distal portion 40 of approximately symmetrical shape and length. Alternate embodiments may increase the length of either the proximal portion 30 or the distal portion 40, to create an asymmetrical profile.

The eccentric enlarged abrading head 28 has a center of mass that is spaced radially away from the longitudinal rotational axis 21 of the drive shaft 20. As will be described in greater detail below, offsetting the center of mass from the drive shaft's axis of rotation 21 provides the enlarged abrading head 28 with an eccentricity that permits it to open an artery to a diameter substantially larger through orbital motion, discussed further infra, than the nominal diameter of the enlarged eccentric abrading head 28, preferably the opened diameter is at least twice as large as the nominal resting diameter of the enlarged eccentric abrading head 28.

Additional variations of the eccentric enlarged abrading head 28 are possible, including an arrangement whereby the wire turns of the drive shaft are enlarged on one side of the drive shaft but not the opposing side, creating an offset of the center of mass from the axis of rotation 21. This arrangement is disclosed within U.S. Pat. No. 6,494,890 to Shturman, the entire contents of which is hereby incorporated herein by reference. The significant part of the eccentric enlarged abrading head 28 of the present invention and its various embodiments is that eccentricity is created, i.e., that the center of mass of the eccentric enlarged abrading head is offset from the axis of rotation of the drive shaft. Such eccentricity drives an orbital pattern of rotation for the eccentric enlarged abrading head 28 as will be discussed further and which is a significant element of the various embodiments of the present invention.

Accordingly, it should be understood that, as used herein, the word "eccentric" is defined and used herein to refer to either a difference in location between the geometric center of the enlarged abrading head 28 and the rotational axis 21 of the drive shaft 20, or to a difference in location between the center of mass 29 of the enlarged abrading head 28 and the rotational axis 21 of the drive shaft 20. Either such difference, at the proper rotational speeds, will enable the eccentric enlarged abrading head 28 to open a stenosis to a diameter substantially greater than the nominal diameter of the eccentric enlarged abrading head 28. Moreover, for an eccentric enlarged abrading head 28 having a shape that is not a regular geometric shape, the concept of "geometric center" can be approximated by locating the mid-point of the longest chord which is drawn through the rotational axis 21 of the drive shaft 28 and connects two points on a perimeter of a transverse cross-section taken at a position where the perimeter of the eccentric enlarged abrading head 28 has its maximum length.

The abrading head 28 of the therapeutic agent delivery device of the invention may be constructed of stainless steel, tungsten, titanium or similar material. The abrading head 28 may be a single piece unitary construction or, alternatively, may be an assembly of two or more abrading head components fitted and fixed together to achieve the objects of the present invention.

The extent to which a stenosis in an artery can be opened to a diameter larger than the nominal diameter of the eccentric enlarged abrading head of the present invention depends on several parameters, including the shape of the eccentric enlarged abrading head, the mass of the eccentric enlarged abrading head, the distribution of that mass and, therefore, the location of the center of mass within the abrading head with respect to the rotational axis of the drive shaft, and the speed of rotation.

The speed of rotation is a significant factor in determining the centrifugal force with which the tissue removing surface 37 of the eccentric abrading head 28 is pressed against the stenotic tissue, thereby permitting the operator to control the rate of tissue removal. Control of the rotational speed of the eccentric abrading head 28 also allows, to some extent, control over the maximum diameter to which the device will open a stenosis. Applicants have also found that the ability to reliably control the force with which the tissue removing surface is pressed against the stenotic tissue not only permits the operator to better control the rate of tissue removal but also provides better control of the size of the particles being removed. Control of the rotational speed of the eccentric abrading head 28 also allows control over the centrifugal forces generated radially outwardly from the rotating abrading head 28. As applied to the present invention, this control of centrifugal forces allows control of efficiency of driving therapeutic agents radially from the point of release and toward the lumen/biological conduit wall.

Figure 3:
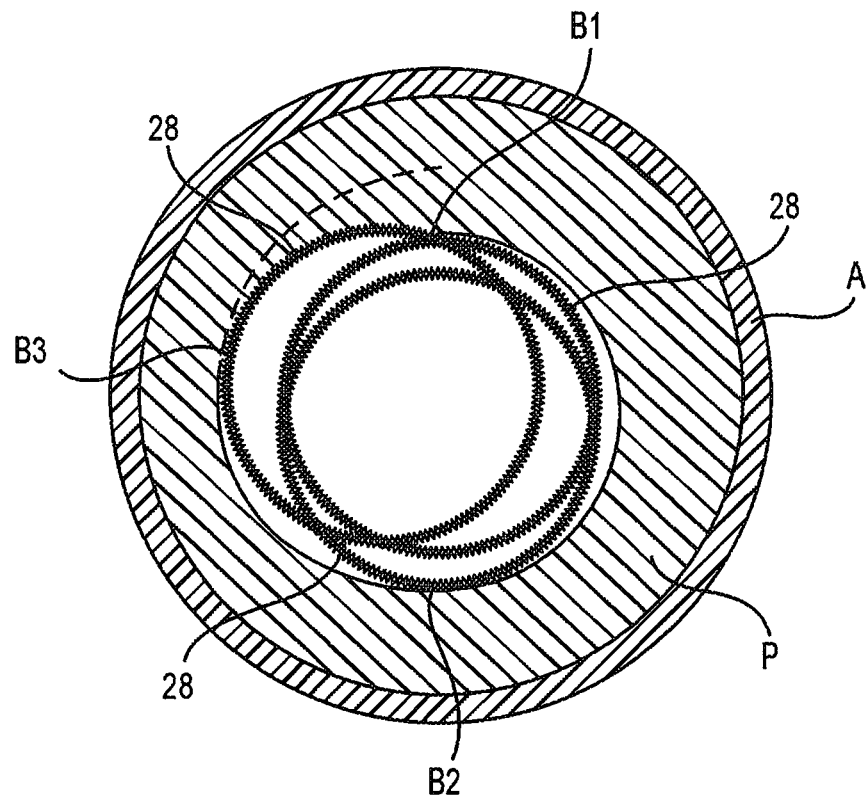
FIG. 3 is a transverse cross-sectional view illustrating three different positions of the rapidly rotating eccentric enlarged abrading head of a high-speed rotational atherectomy device of the invention.
Figure 4:
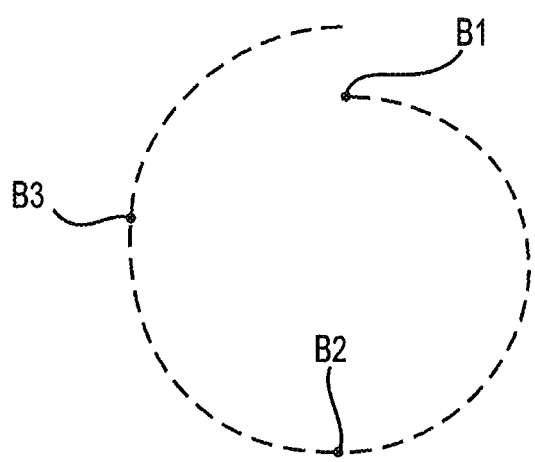
FIG. 4 is a schematic view corresponding to the three positions of the rapidly rotating eccentric enlarged abrading head illustrated in FIG. 4.

FIGS. 3 and 4 illustrate the generally spiral orbital path taken by various embodiments of the eccentric abrading head 28 of the present invention, the abrading head 28 shown relative to the guide wire 15 over which the abrading head 28 has been advanced. The pitch of the spiral path in FIGS. 3 and 4 is exaggerated for illustrative purposes—in reality, each spiral path of the eccentric abrading head 28 removes only a very thin layer of tissue via the abrading head 28, and many, many such spiral passes are made by the eccentric enlarged abrading head 28 as the device is repeatedly moved forward and backward across the stenosis to fully open the stenosis. FIGS. 3 and 4 shows schematically three different rotational positions of the eccentric enlarged abrading head 28 of a rotational atherectomy device of the invention. At each position the abrasive surface of the eccentric enlarged abrading head 28 contacts the plaque "P" to be removed—the three positions are identified by three different points of contact with the plaque "P", those points being designated in the drawing as points B1, B2, and B3. Notice that at each point it is generally the same portion of the abrasive surface of the eccentric enlarged abrading head 28 that contacts the tissue—the portion of the tissue removing surface 37 that is radially most distant from the rotational axis of the drive shaft.

Although not wishing to be constrained to any particular theory of operation, applicants believe that offsetting the center of mass from the axis of rotation 21 produces an "orbital" movement of the eccentric abrading head 28, the diameter of the "orbit" being controllable by varying, inter alia, the rotational speed of the drive shaft 20. Applicants have empirically demonstrated that by varying the rotational speed of the drive shaft 20 one can control the centrifugal force urging the tissue removing surface 37 of the eccentric abrading head 28 against the surface of the stenosis. The centrifugal force can be determined according to the formula:

$$F_c = m\Delta x(\pi n/30)^2$$

where $F_c$ is the centrifugal force, m is the mass of the eccentric enlarged abrading head, $\Delta x$ is the distance between the center of mass of the eccentric abrading head 28 and the rotational axis 21 of the drive shaft 20, and n is the rotational speed in revolutions per minute (rpm). Controlling this force $F_c$ provides control over the rapidity with which tissue is removed, control over the maximum diameter to which the device will open a stenosis, and improved control over the particle size of the tissue being removed. In addition, this control of centrifugal forces allows control of efficiency of driving therapeutic agents radially from the point of release and toward the lumen/biological conduit wall.

Figure 5:
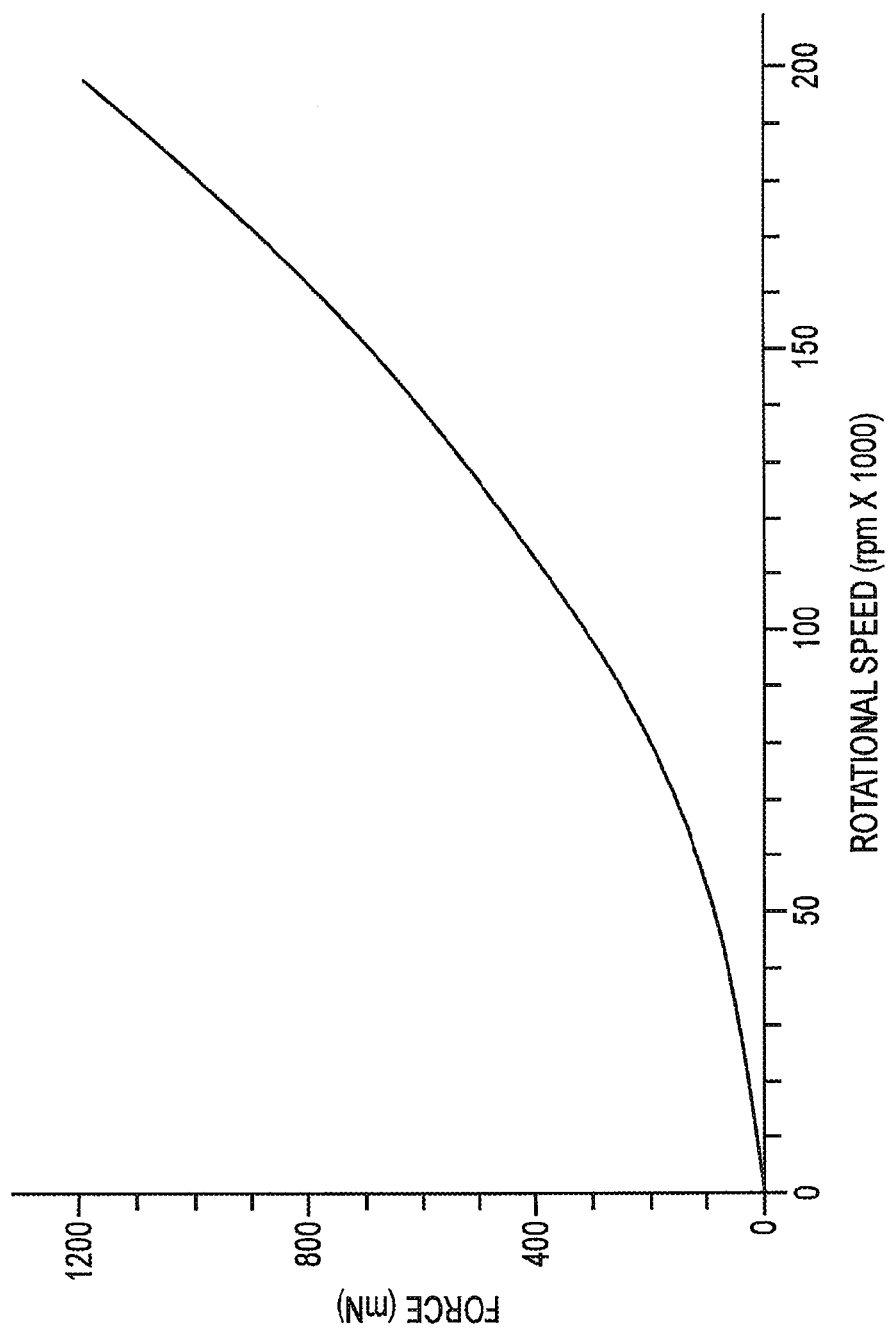
FIG. 5 is a graph of centrifugal force generated by an enlarged eccentric abrading head of a high-speed rotational atherectomy device of the invention in relation to the rotational speed of the eccentric abrading head.

The graph shown in FIG. 5 illustrates calculations of the maximum centrifugal force $F_c$ with which an exemplary eccentric abrading head 28, having a maximum diameter of about 1.75 mm, can press against a surface of a stenosis at rotational speeds up to about 200,000 rpm. Controlling this force $F_c$ provides control over the rapidity with which tissue is removed, control over the maximum diameter to which the device will open a stenosis, and improved control over the particle size of the tissue being removed. Utilizing this force $F_c$ to assist in the delivery of therapeutic substances delivered into the orbital path of the high-speed rotational eccentric abrading head 28 to the subject wall of the lumen or biological conduit is one focus of the present invention in its various embodiments.

Figure 6:
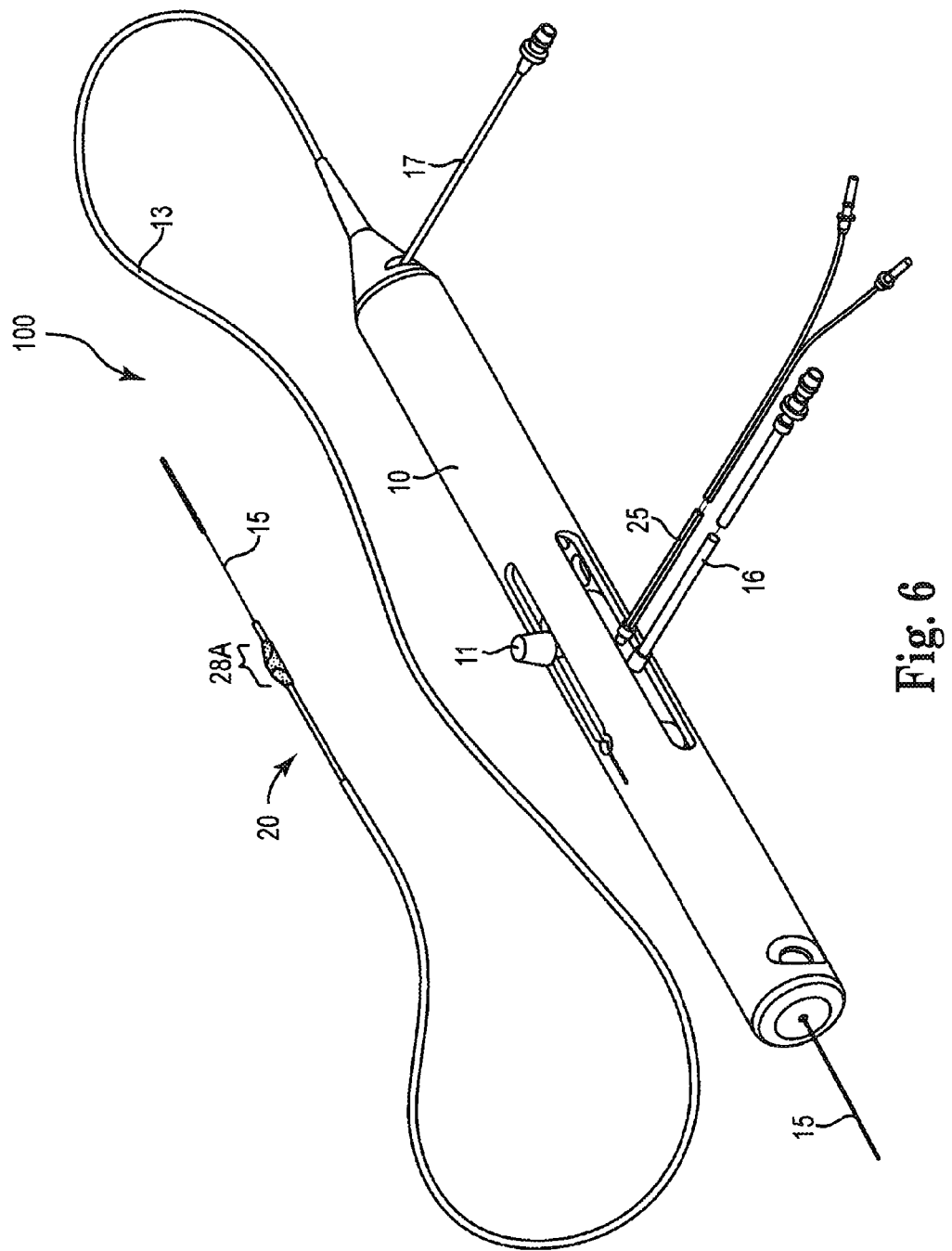
FIG. 6 is a perspective view of one embodiment of a therapeutic agent delivery system comprising an eccentric abrading head of a rotational atherectomy device of the invention.
Figure 7:
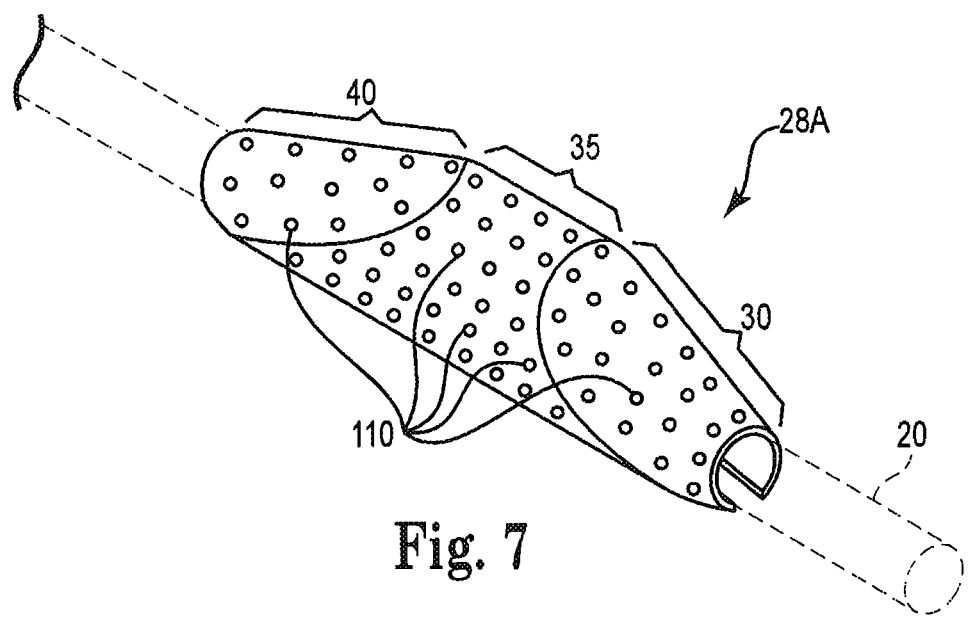
FIG. 7 is a perspective view of one embodiment of the eccentric abrading head of FIG. 6.
Figure 8:
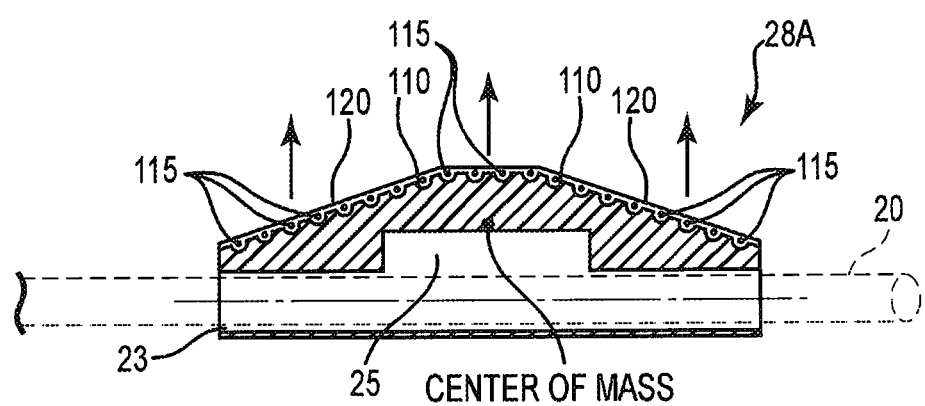
FIG. 8 is a longitudinal cross-sectional view of the eccentric abrading head of FIG. 6.

Turning now to FIGS. 6-8, one embodiment of the therapeutic agent delivery system of the present invention will be described. FIG. 6 illustrates a therapeutic delivery system 100 with the same elements as described in connection with FIG. 1 supra, with one exception: the eccentric abrading head 28A comprises at least one, and preferably a plurality, of compartments 110 in its housing. The compartment(s) 110 are disposed on one or more of the proximal portion 30, the intermediate portion 35 and the distal portion 40, as is best seen in FIGS. 7 and 8. The compartment(s) 110 are pre-filled with at least one therapeutic agent 115 and then the external surface of the eccentric abrading head 28A is coated 120 so as to temporarily seal the compartment(s) 110 with the at least one therapeutic agent 115 therein. Such a coating seal may be slowly worn down during the atherectomy procedure, e.g., a polyethylene or similar material such that when the coating is worn down, the compartment(s) 110 are opened, exposing the at least one therapeutic agent(s) 115 therein to the lumen or biological conduit. Other coatings 110 are well known in the art and may comprise coating that slowly dissolve on exposure to liquid and the like. Each such coating 110 is within the scope of the present invention. Alternatively, instead of coating the external surface of the eccentric abrading head 28A to cover the compartment(s) 110, the individual compartment(s) 110 may be coated and sealed, whereby the coating may slowly wear down and/or dissolve during the atherectomy procedure.

The coating 120 is preferably removed from the compartment(s) 110 during the atherectomy procedure. Thus, the radial forces generated by the orbital motion and centrifugal forces of the eccentric abrading head 28A, with its center of mass offset from the rotational axis 21 of the drive shaft 20, will work to eject the at least one therapeutic agent 115 out of the compartment(s) 110 in a generally radial direction as illustrated by arrows in FIG. 8. The continued exposure of the ejected, released therapeutic agent(s) 115 to the orbiting high-speed rotational eccentric abrading head 28A further exposes the released therapeutic agent(s) 115 to the radial forces generated by the head 28A. These radial forces, combined with physical impact of some of the therapeutic agents 115 which will tend to throw the agent(s) outward radially, drivingly urge the therapeutic agent(s) radially outward toward the wall of subject lumen or biological conduit. Ultimately, these forces will cause the therapeutic agent(s) to impact the wall of the lumen or biological conduit, a significant amount of which will impact the wall with sufficient force so as to be applied to the wall where the therapeutic value of the impacted therapeutic agent(s) is realized. This process is described in some detail by Ramazani-Rend, et al., "Experimental and numerical investigation of orbital atherectomy: absence of cavitation", J. Biomedical Science and Engineering, 2010, 3, 1108-1116, the entire contents of which are hereby incorporated by reference. Since the atherectomy procedure is performed before application of the therapeutic agent 115, the lumen or biological conduit wall is newly sanded and, therefore, uniquely receptive to the radially driven therapeutic agent 115.

Figure 9:
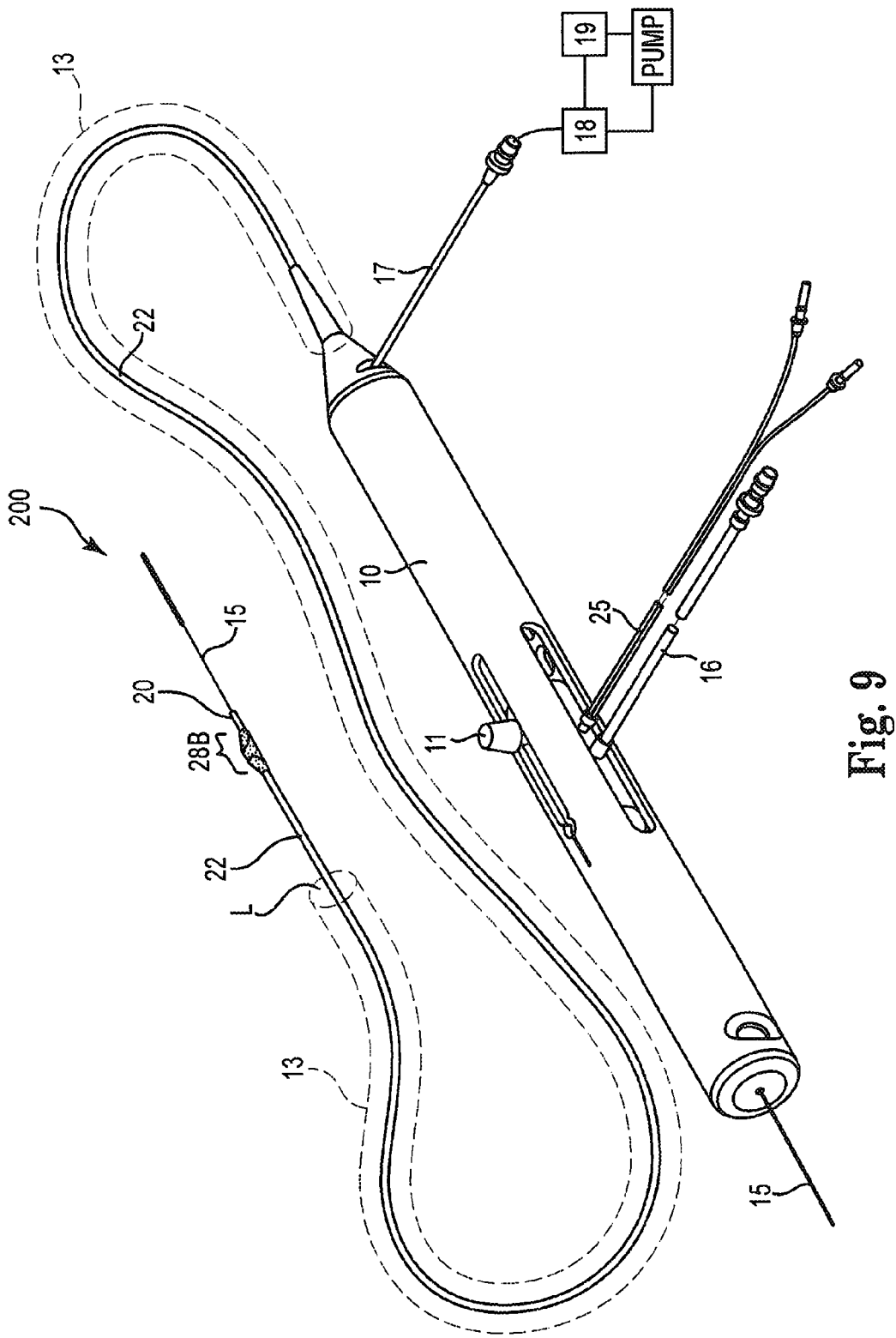
FIG. 9 is a perspective view of one embodiment of a therapeutic agent delivery system comprising an eccentric abrading head of a rotational atherectomy device of the invention.
Figure 10:
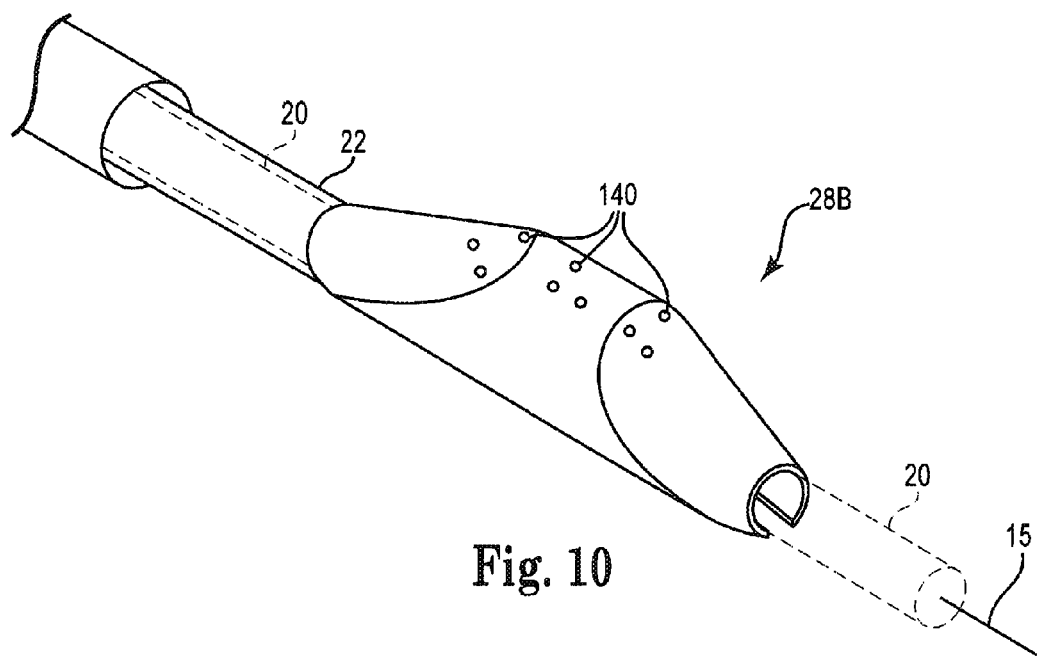
FIG. 10 is a partial cutaway view of one the therapeutic agent delivery system of the present invention.
Figure 11:
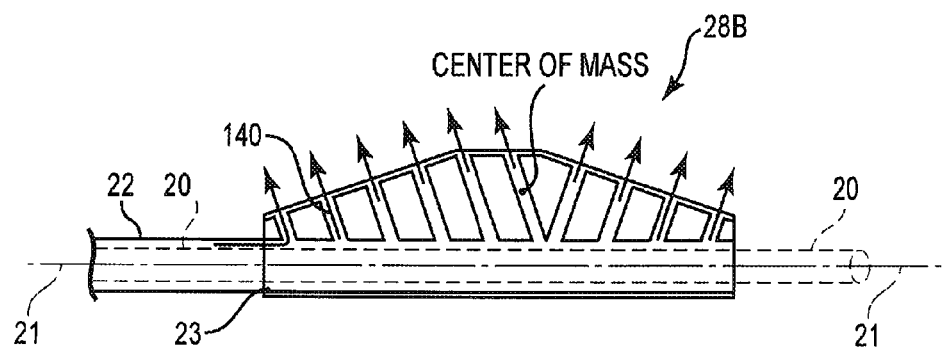
FIG. 11 is a longitudinal cross-sectional and cutaway view of the eccentric abrading head of FIG. 9.

Another embodiment of the present invention is illustrated in FIGS. 9-11. FIG. 9 illustrates one embodiment of a therapeutic agent delivery system 200 of the present invention comprising a high-speed rotational atherectomy system. The device includes a handle portion 10, an elongated, flexible drive shaft 20 having an eccentric enlarged abrading head 28B comprising at least one spray hole 140, and an elongated catheter 13, illustrated with dashed lines, extending distally from the handle portion 10. The drive shaft 20 is constructed from helically coiled wire as is known in the art and the abrading head 28B is fixedly attached thereto. The catheter 13 has a lumen L within which the drive shaft 20 is slidably disposed and further comprises a distal end. A therapeutic substance delivery sheath 22, comprising a lumen therethrough is also disposed within the lumen L of catheter 13, the lumen of therapeutic substance delivery sheath 22 is in fluid communication with the at least one spray hole 140 of eccentric abrading head 28B.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. Details regarding such handles and associated instrumentation are well known in the industry. The handle 10 also desirably includes a control knob 11 for advancing and retracting the turbine and drive shaft 20 with respect to the catheter 13 and the body of the handle. Actuation of pump for introducing therapeutic substance(s) into the drive shaft lumen may be controlled by a separate controller knob located on the handle 10 or by a separate controller mounted in operative communication with the pump and/or therapeutic substance reservoir 18. It will be readily apparent to the skilled artisan that the dosing of the therapeutic substance(s), advanced through the therapeutic substance delivery sheath 22 from the therapeutic substance reservoir 18 and to the spray hole(s) 140 of eccentric abrading head 28B and subsequent pressured release therefrom prior to high-speed rotation of the abrading head 28 and/or during high-speed rotation of the abrading head 28, may be monitored and controlled in many ways. For example, only a known dosage of therapeutic substance(s) may be added to the therapeutic substance reservoir 18 and/or a gauge may be employed to assist the operator in monitoring the amount of therapeutic substance moving through fluid supply line 17. A controller 19, as is well known in the art, may be in operative communication with therapeutic substance reservoir 18 and pump for controlling volume and rate of flow therefrom. All such known methods of monitoring the amount of fluid flow are within the scope of the present invention.

In operation, the high-speed atherectomy system is activated, causing high-speed rotation of the drive shaft 20. The operator may then actuate the therapeutic delivery pumping by activating the pump and initiating the pumping of the at least one therapeutic substance through the therapeutic agent delivery sheath 22 which, as illustrated comprises a lumen defined between the space of the rotating drive shaft 20, slidably and rotatably disposed within the lumen of the therapeutic agent delivery sheath 22 in a concentric arrangement, and the therapeutic agent delivery sheath 22; the therapeutic agent moves distally through this lumen. In this embodiment, the therapeutic agent delivery sheath 22 does not rotate, rather the drive shaft 20 rotates within its lumen. An alternative embodiment for the therapeutic agent delivery sheath 22 may comprise the sheath 22 and the drive shaft 20 in a non-concentric relationship as in the illustrated embodiment. Rather, sheath 22 and drive shaft 20 occupy separate spaces within catheter lumen. Further alternate embodiments for delivery of the therapeutic agent(s) to the eccentric abrading head 28B may present themselves to the skilled artisan, each such embodiment is within the scope of the present invention.

In all embodiments, ultimately, the therapeutic agent reaches the lumen 23 within eccentric abrading head 28B. Because the abrading head 28B comprises a center of mass that is offset from the rotational axis 21 of the drive shaft 20, the high-speed rotation of eccentric abrading head 28B comprises an orbital motion as described above. This creates, also as described above, strong centrifugal forces which, combined with the pressuring of the therapeutic agent(s) along the lumen of the therapeutic agent delivery sheath 22, results in movement of the at least one therapeutic agent through the spray holes 140 which are in fluid communication with the lumen 23 of eccentric abrading head 28B. As illustrated, the spray holes 140 serve as a conduit out of the eccentric abrading head 28B and into the lumen of the vessel or biological conduit. As illustrated, strong radial forces, generated in part by the initial ejection forces from the spray holes 140 and in part from the strong centrifugal radial forces generated by the orbital motion of the high-speed rotation of the eccentric abrading head 28B, drivingly urge the therapeutic agent radially outward and toward the wall of the subject lumen or biological conduit. Ultimately, the therapeutic agent(s) is driven into and applied to the wall to provide its desired therapeutic effect. Since the atherectomy procedure is performed before application of the therapeutic agent, the lumen or biological conduit wall is newly sanded and, therefore, uniquely receptive to the radially driven therapeutic agent.

Figure 12:
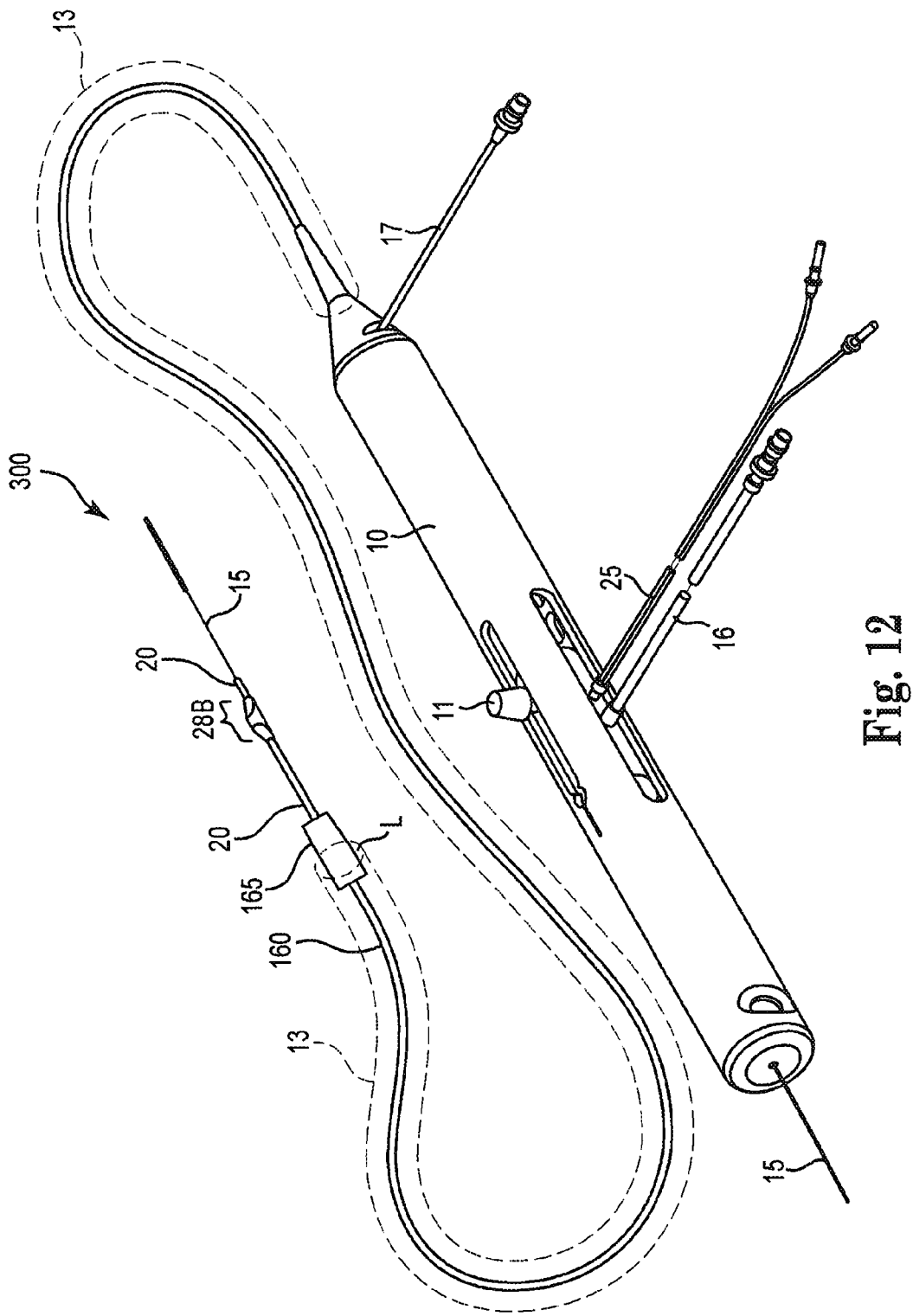
FIG. 12 is a perspective view of one embodiment of a therapeutic agent delivery system comprising a rotational atherectomy device of the invention.
Figure 13:
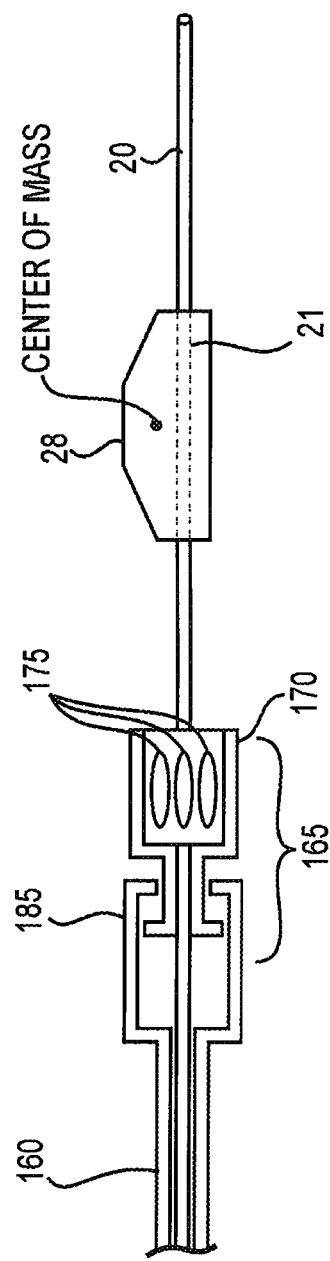
FIG. 13 is a partial cutaway cross-sectional view of the therapeutic agent delivery system of FIG. 12.

Turning now to FIGS. 12 and 13, another embodiment of the therapeutic agent delivery system of the present invention is illustrated. FIG. 12 illustrates one embodiment of a therapeutic agent delivery system of the present invention comprising a high-speed rotational atherectomy system. The device includes a handle portion 10, an elongated, flexible drive shaft 20 having an eccentric enlarged abrading head 28 as described in connection with FIGS. 1, 2A-2C, and an elongated catheter 13, illustrated with dashed lines, extending distally from the handle portion 10. The drive shaft 20 is constructed from helically coiled wire as is known in the art and the abrading head 28 is fixedly attached thereto. The catheter 13 has a lumen L within which a non-rotating sheath 160 is disposed, the sheath 160 comprising a distal retractable assembly 165. The non-rotating sheath 160 comprises a lumen therethrough within which the drive shaft 20 is slidably and rotatably disposed.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. Details regarding such handles and associated instrumentation are well known in the industry. The handle 10 also desirably includes a control knob 11 for advancing and retracting the turbine and drive shaft 20 with respect to the catheter 13 and the body of the handle.

The retractable assembly 165 of system 300 comprises a distal housing 170 comprising at least one, and preferably more than one, hollowed out compartment 175. The hollowed out compartment(s) 175 are preloaded with a predetermined amount of at least one therapeutic agent(s) prior to insertion of the therapeutic delivery system 300 into the patient's lumen or biological conduit. The agent(s) may be in liquid form, frozen or encapsulated, wherein the frozen agent(s) will be allowed to thaw before released into the lumen or biological conduit and the capsule will be dissolvable in liquid in order to release the agent(s) into the lumen or conduit. One side of the distal housing 170 is illustrated. As the skilled artisan will recognize, two or more, sides of the distal housing 170 may comprise compartment(s) 175. The distal housing is illustrated as a rectangle, though other shapes may be utilized.

The retractable assembly 165 further comprises a retractable sheath 160 which comprises a distal end having an enlarged region 185 within which the distal housing 170 slidably fits, the distal housing 170 being complementary to the shape of the enlarged region 185, and wherein and whereby the hollowed out compartment(s) 175 containing the therapeutic agents, are protected during insertion and during the atherectomy procedure. The enlarged region 185 encapsulates the distal housing 170 to the degree where the hollowed out compartment(s) 175 are not exposed to the lumen environment until the retractable sheath 160 is retracted proximally, thereby removing the enlarged region 185 from the distal housing 170. Such retraction of the retractable sheath 160 thus exposes the therapeutic agent(s) held preloaded into the hollowed out compartment(s) 175 to the lumen environment.

In operation, the guide wire 15, drive shaft 20 comprising the eccentric abrading head 28 thereon are positioned hear the occlusion. The non-rotating sheath 160 is also inserted in the lumen or biological conduit, with the retractable assembly 165, including preloaded hollowed out compartment(s) 175, positioned distal to the eccentric abrading head. High-speed atherectomy is initiated and, at some point in the procedure, the operator may determine to retract the retractable sheath 160 to release the therapeutic agent(s) from the hollowed out compartment(s) 175. As described above, this retraction results in the enlarged region 185 moving distally away from distal housing 170, thereby exposing the therapeutic agent(s) held therein in the hollowed out compartment(s) 175 to the lumen or conduit environment.

Ultimately, the therapeutic agent disperses out of the hollowed out compartment(s) 175 and into the lumen or conduit within. Because the abrading head 28 comprises a center of mass that is offset from the rotational axis 21 of the drive shaft 20, the high-speed rotation of eccentric abrading head 28, as discussed above in connection with FIGS. 1, 2A-2C, and 3-5, comprises an orbital motion as described above. This creates, also as described above, strong centrifugal forces which will entrain the dispersing therapeutic agent(s), driving the agent(s) radially outward toward the wall of the lumen or biological conduit. These strong radial forces will drivingly urge the therapeutic agent radially outward and toward the wall of the subject lumen or biological conduit. Ultimately, the therapeutic agent(s) is driven into and applied to the wall to provide its desired therapeutic effect. Since the atherectomy procedure is performed before application of the therapeutic agent, the lumen or biological conduit wall is newly sanded and, therefore, uniquely receptive to the radially driven therapeutic agent.

Figure 14:
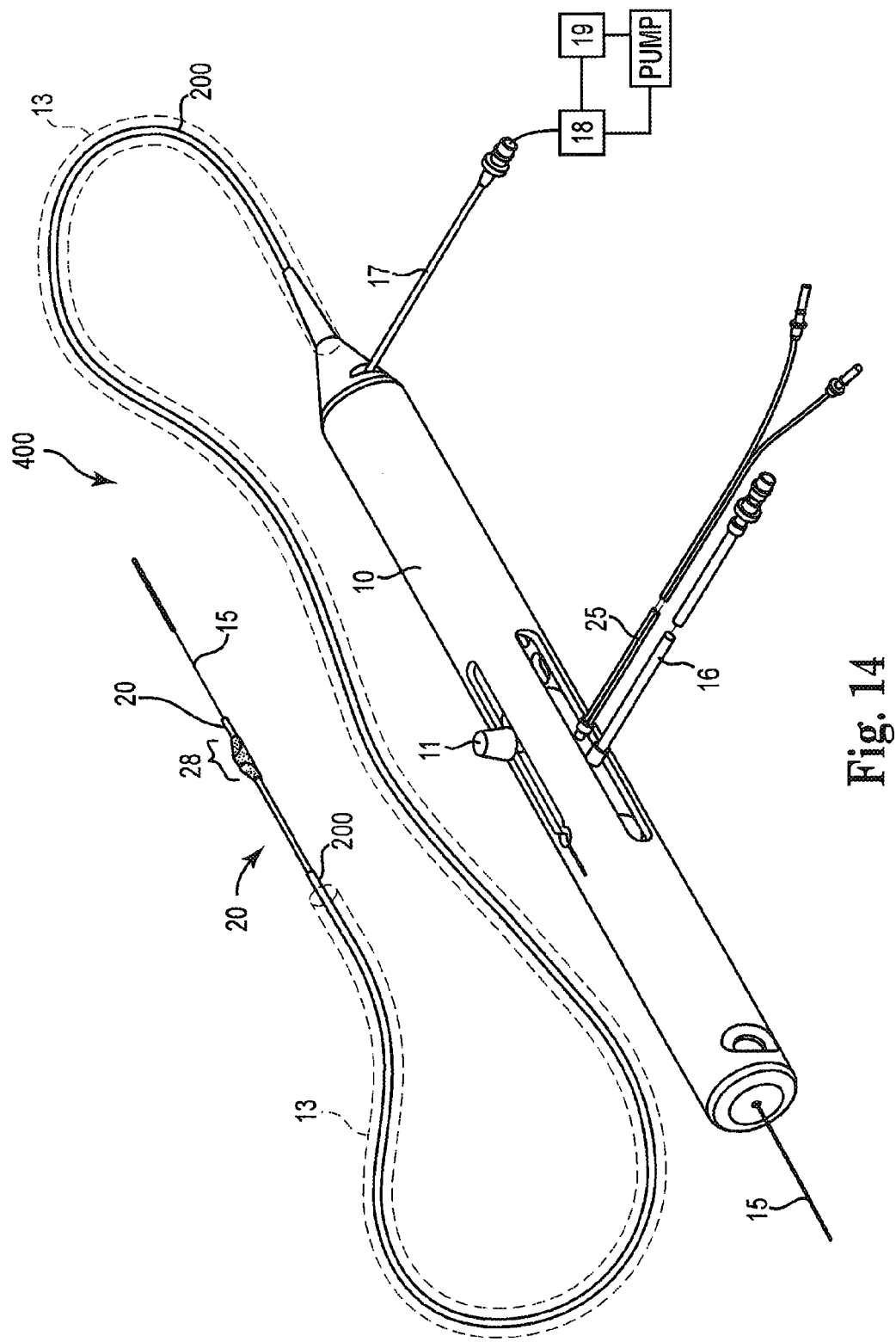
FIG. 14 is a perspective view of one embodiment of a therapeutic agent delivery system comprising an eccentric abrading head of a rotational atherectomy device of the invention.
Figure 15:
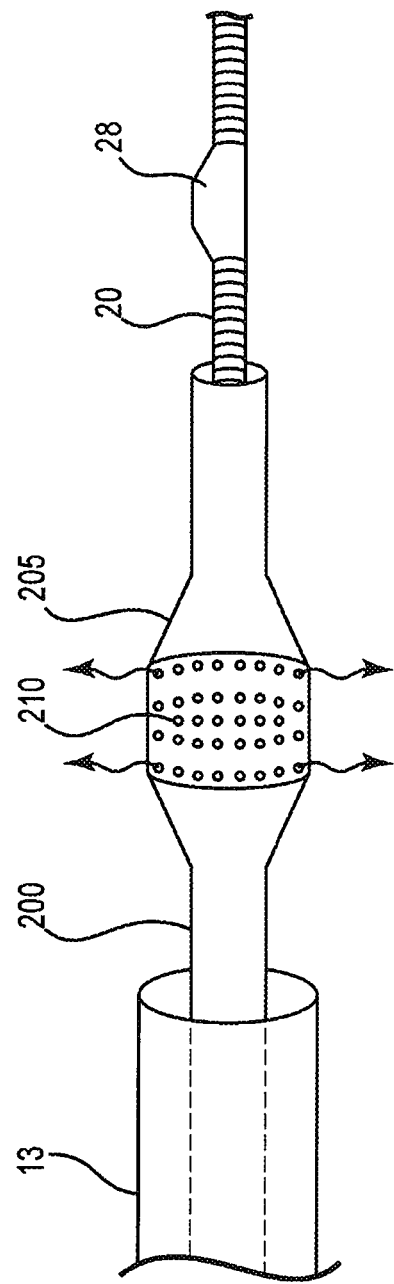
FIG. 15 is a partial cutaway cross-sectional view of the therapeutic agent delivery system of FIG. 14.

Turning now to FIGS. 14 and 15, another embodiment of a therapeutic agent delivery system 400 of the present invention comprising a high-speed rotational atherectomy system. The device includes a handle portion 10, a therapeutic agent delivery sheath 200 comprising a lumen therethrough, an elongated, flexible drive shaft 20 having an eccentric enlarged abrading head 28, as discussed and described supra slidably and rotatably disposed within sheath 200, and an elongated catheter 13, illustrated with dashed lines, extending distally from the handle portion 10. The drive shaft 20 is constructed from helically coiled wire as is known in the art and the abrading head 28 is fixedly attached thereto. The catheter 13 has a lumen L within which the delivery sheath 200 is slidably disposed and further comprises a distal end. Therapeutic agent delivery sheath 200 further comprises an inflatable balloon 205 thereon, the balloon 205 comprising a plurality of pores 210 for ejection of the therapeutic agent therefrom, the pores 210 in fluid communication with lumen of sheath 200 and with therapeutic agent reservoir 18.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. Details regarding such handles and associated instrumentation are well known in the industry. The handle 10 also desirably includes a control knob 11 for advancing and retracting the turbine and drive shaft 20 with respect to the catheter 13 and the body of the handle. Actuation of pump for introducing therapeutic substance(s) into the lumen of sheath 200 may be controlled by a separate controller knob located on the handle 10 or by a separate controller 19 mounted in operative communication with the pump and/or therapeutic substance reservoir 18. It will be readily apparent to the skilled artisan that the dosing of the therapeutic substance(s), advanced through the therapeutic agent delivery sheath 200 from the therapeutic substance reservoir 18 and to the pores 210 of balloon 205 and subsequent pressured release therefrom prior to high-speed rotation of the abrading head 28 and/or during high-speed rotation of the abrading head 28, may be monitored and controlled in many ways. For example, only a known dosage of therapeutic substance(s) may be added to the therapeutic substance reservoir 18 and/or a gauge may be employed to assist the operator in monitoring the amount of therapeutic substance moving through fluid supply line 17. A controller 19, as is well known in the art, may be in operative communication with therapeutic substance reservoir 18 and pump for controlling volume and rate of flow therefrom. All such known methods of monitoring the amount of fluid flow are within the scope of the present invention.

In operation, the therapeutic delivery system 400 is positioned in the patient's lumen, in particular, the eccentric abrading head 28 is positioned proximate to the occlusion to be abraded and the high-speed atherectomy system is activated, causing high-speed rotation of the drive shaft 20, with orbital motion of the eccentric abrading head 28 as described supra. Once the vessel wall is cleared of the occlusion, sheath 200 is translated distally to expose the deflated balloon 205 to the lumen, i.e., moving the balloon 205 out of the lumen of the catheter 13 so that it may be inflated using inflation means and media well known in the art. Once the balloon 205 is inflated, the operator may then actuate the therapeutic delivery pumping by activating the pump and initiating the pumping of the at least one therapeutic substance through the lumen of the therapeutic agent delivery sheath 200; the therapeutic agent moves distally through this lumen. In this embodiment, the therapeutic agent delivery sheath 200 does not rotate, rather the drive shaft 20 rotates within the lumen of the sheath 200. An alternative embodiment for the therapeutic agent delivery sheath 200 may comprise the sheath 200 and the drive shaft 20 in a non-concentric relationship. Rather, sheath 200 and drive shaft 20 occupy separate spaces within the lumen of catheter 13 in this alternative embodiment.

In all cases, the movement of the therapeutic agent(s) distally through lumen of sheath 200 ultimately reaches the inflatable balloon 205 and is pressured to exit the balloon 205 through pores 210, where the agent(s) encounters the centrifugal forces and impact forces described supra. The therapeutic agent(s) are driven radially outwardly by these forces, toward the wall of vessel where the agent(s) are impacted and positioned for therapy.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy system for delivering at least one therapeutic agent to a biological lumen wall during a high-speed rotation atherectomy procedure within the biological lumen, comprising:
   a guide wire having a maximum diameter less than the diameter of the biological lumen;
   a flexible elongated, rotatable drive shaft advanceable over the guide wire, the drive shaft having a rotational axis;
   an eccentric abrading head comprising an external surface and attached to the drive shaft, the eccentric abrading head comprising a center of mass that is offset from the rotational axis of the drive shaft;
   a therapeutic agent reservoir;
   a fluid supply line in fluid communication with the therapeutic agent reservoir;
   a pump in operative connection with the therapeutic agent reservoir;
   a controller in operative communication with the pump and the therapeutic agent reservoir;
   a non-rotating therapeutic agent delivery sheath, the sheath comprising a lumen therethrough, the drive shaft slidably and rotatably disposed in the sheath lumen, the non-rotating therapeutic agent delivery sheath further comprising an inflatable balloon arranged on a distal end thereof, the lumen of the therapeutic agent delivery sheath in fluid communication with the therapeutic agent reservoir and the inflatable balloon, and the inflatable balloon comprising a plurality of pores in direct fluid communication with the lumen of the therapeutic agent delivery sheath;
   a catheter disposed over the sheath; and
   means for drivingly urging the at least one therapeutic agent radially outwardly away from the eccentric abrading head and into the lumen wall.

2. The system of claim 1, wherein the means for drivingly urging the at least one therapeutic agent radially outwardly away from the eccentric abrading head and into the lumen wall comprises centrifugal forces generated by an orbital motion achieved by the eccentric abrading head during high-speed rotation.

3. The system of claim 1, wherein the means for drivingly urging the at least one therapeutic agent radially outwardly away from the eccentric abrading head and into the lumen wall comprises radially outward impact forces generated by the impact of the therapeutic agent and the orbital motion of the eccentric abrading head during high speed rotation.

* * * * *